(12) United States Patent
Woodford et al.

(10) Patent No.: US 7,716,962 B2
(45) Date of Patent: May 18, 2010

(54) METHOD OF CALIBRATING A GAS SENSOR

(75) Inventors: Malcolm Woodford, Southampton (GB); John Darby, Southampton (GB)

(73) Assignee: Life Safety Distribution AG, Uster (CH)

( * ) Notice: Subject to any disclaimer, the term of this patent is extended or adjusted under 35 U.S.C. 154(b) by 353 days.

(21) Appl. No.: 12/017,860

(22) Filed: Jan. 22, 2008

(65) Prior Publication Data
US 2008/0173065 A1    Jul. 24, 2008

(30) Foreign Application Priority Data
Jan. 22, 2007   (GB) ................................ 0701180.2

(51) Int. Cl.
*G01N 21/00* (2006.01)
(52) U.S. Cl. ...................................... 73/1.06
(58) Field of Classification Search .................. 73/1.06, 73/1.59
See application file for complete search history.

(56) References Cited

U.S. PATENT DOCUMENTS 4,423,487 A * 12/1983 Buckenham et al. ........ 702/182
5,457,320 A * 10/1995 Eckles et al. ................. 250/345

FOREIGN PATENT DOCUMENTS

WO    WO 2005/054827 A1    6/2005

OTHER PUBLICATIONS

R. Van Ewyk et al., "Infrared Gas Detection", *Techniques and Mechanisms in Gas Sensing*, Eds P. T. Moseley, J. O. W. Norris and D. E. Wilson, Adam Hilger, 1991, pp. 234-259.

* cited by examiner

*Primary Examiner*—Hezron Williams
*Assistant Examiner*—Tamiko D Bellamy
(74) *Attorney, Agent, or Firm*—Husch Blackwell Sanders Welsh & Katz

(57) ABSTRACT

A method of calibrating a gas sensor that generates an output related to the concentration of a sensed gas, the method comprising:
i) obtaining the value of said output or a related value at each of a set of known values of a first variable and at each of a set of known values of a second variable, one of the variables being gas concentration;
ii) for each value of said second variable, determining a first best fit function relating said output or related value to the first variable, each best fit function utilizing at least one coefficient whose value is determined;
iii) for the, or the corresponding, coefficient values from each of the first best fit functions, determining a second best fit function relating said coefficient to the second variable, and replacing the coefficient values in the first best fit functions by the second best fit function, and,
iv) repeating step iii) for each further coefficient, if any, in the first best fit functions so as to generate a final function relating said output or related value and said first and second variables.

10 Claims, 4 Drawing Sheets

METHOD OF CALIBRATING A GAS SENSOR

FIELD OF THE INVENTION

The invention relates to a method of calibrating a gas sensor which generates an output related to the concentration of a sensed gas.

DESCRIPTION OF THE PRIOR ART

It is important to recognise that the reference to an output related to gas concentration is intended to include sensors whose output is directly related to concentration as well as those whose output is directly related to the partial pressure of gas. For example, an electrochemical oxygen sensor provided with a capillary diffusion barrier (i.e. one in which intermolecular collisions dominate and wall collisions are insignificant) provides a volume concentration measurement, whereas a similar device fitted with a Knudsen diffusion barrier (a membrane whose pore size is much less than the molecular mean free path) responds to partial pressure. Infra red (IR) gas sensors are also partial pressure sensors.

Users of gas sensors ideally require that the output of the device should respond only to the measurand of interest and have no significant dependence upon other environmental variables such as ambient temperature. However, most sensing technologies suffer to some degree from problems caused by interferences of this type.

There are two fundamentally different ways in which an interfering variable may impact the output of a gas sensor. In the first case, the variable may alter a property of the gas directly, whilst having no or negligible impact upon the operation and performance of the sensor components themselves. For example, in an IR gas sensor, small changes in ambient pressure have no measurable effect upon the sensor hardware performance, but significantly alter the readings obtained by virtue of placing more or less absorbing molecules in the gas path. Thus, a sensor output calibrated at one pressure will show major errors when used at a different pressure unless compensation is applied. It is a characteristic of such effects that they can be considered generic over all sensors of the same design (or gas type) and therefore the corrections required are relatively easily handled by a generic method.

The second case is where the interfering variable affects one or more properties of the sensor itself. This may happen in isolation from any generic effects, or in addition to them. An example is the effect of temperature upon an IR gas sensor. In this case, there are changes in the fundamental absorption spectrum of the gas (a generic effect) but these are typically very small when compared with the impact of temperature upon optical filter, detector, source, electronic and mechanical components in the device. Although good design limits the impact, in practise significant temperature coefficients remain. Since these derive from components and assemblies which themselves exhibit variability, the temperature effects differ between sensors of nominally the same design. If the sensor-to-sensor variation is significant, it is essential to apply a sensor-specific correction in order to obtain high levels of measurement accuracy.

The present invention is concerned with the second case. For example, thermal sensors such as pellistors for the detection of flammable gases naturally exhibit a dependence upon temperature. In electrochemical gas sensors the key electrocatalytic reactions are often activated and so their rates exhibit temperature sensitivity. Knudsen, gas and solid phase diffusion processes all exhibit temperature coefficients which must be taken into account when presenting the sensor output in terms of gas concentration.

Wherever possible, sensor designers attempt to alleviate such problems by incorporating compensating elements within the design. The compensator in a pellistor pair or an auxiliary electrode in an amperometric electrochemical sensor may be used to provide at least partial cancellation of undesirable thermal effects.

Another class of gas sensors which may suffer from significant temperature dependence are those based on IR absorption. These often operate in the 3-5 micron wavelength band where many gases of interest exhibit fundamental absorption features which may be selected by an interference filter (although the same principles can be employed in other regions of the electromagnetic spectrum). Most IR detectors exhibit significant changes in output as the ambient temperature varies. It is common to employ a reference channel in such designs, see for example WO 2005/054827. This typically receives radiation along the same light path as the signal channel, but is provided with an optical filter which renders it insensitive to the target species. In addition to compensating for changes in source intensity or general obscuration, such a reference can provide a degree of temperature compensation. More sophisticated systems may employ detectors having a second IR active element attached to each channel but which is shielded from the incoming radiation. This provides means for further improvements in temperature performance, particularly under transient conditions.

Despite the use of good thermal management practices in sensor designs, there is invariably a residual temperature coefficient which must be addressed. Similarly, efforts to compensate for other interferences such as humidity are often inadequate. This results in the need for individual sensor calibrations allowing users to compensate for the particular conditions encountered in their application.

In general, gas sensors have a signal output (or some other value derived from it) with nonlinear dependence on the target gas concentration. This is especially true in IR absorption sensors where the fundamental monochromatic absorption process, described in the ideal case by the Beer Lambert law, leads to a highly nonlinear relationship between absorption and gas concentration. (See, for example, "Infrared Gas Detection", R van Ewyk and B M Willatt, Ch 10 in "Techniques and Mechanisms In Gas Sensing", Eds P T Moseley, J O W Norris and D E Williams, Adam Hilger, 1991). Furthermore, at any fixed gas concentration, the temperature dependence of the output signal (or a useful value derived therefrom) may itself be nonlinear. This leads to a complicated situation in which the provision of accurate calibration data across a wide range of operating concentrations and temperatures is challenging.

In principle, information allowing compensation of the sensor output may be located either in the host instrument or the sensor itself. The size, cost and power consumption of processors, microcontrollers and/or memory required to facilitate such operations are generally less significant in an instrument (where they may multiplex between a number of sensors and perform other key functions such as driving displays) than they would be in a single sensor, but are still not negligible. A drawback of instrument-based calibration is that the sophisticated test and data acquisition systems which may be required are usually only available in central facilities, ruling out field replacement of sensors. Furthermore, it is usually cheaper for the sensor manufacturer to undertake such calibrations on large numbers of sensors in parallel as part of the routine production process.

If sufficient information can be permanently associated with a sensor via hardware such as an EEPROM, then relatively simple field replacement becomes feasible provided the host instrument can acquire and use the data. More intelligent, active sensor modules have also been created (for example commercial products based on the IEEE P1451.0 standard) but there is always a tradeoff to be made between increased sophistication and low cost. The latter requirement tends to dominate in markets for small, portable devices.

It is also important to recognize that in this class of sensors, variation between nominally identical devices can represent a (and often the most) significant source of error. Ideally, the instrument manufacturer wishes to employ a common compensation correction for all sensors of the same design, but the inherent variability of many sensor manufacturing processes mean that this does not provide adequate performance in many applications.

Regardless of the location of the data within the measurement system, there are a range of approaches which may be adopted in providing the required level of compensation. The most obvious (and potentially most accurate) approach is to characterize the output of the sensor across the full measurand and and interference (temperature) ranges. An independent measurement of temperature and a look up table may then provide corrected output data. However, in most cases this requires unacceptably long and detailed calibration procedures (with high associated costs) to provide sufficiently high resolution mapping of the operating space to deliver useful levels of accuracy. Despite the relatively low cost of memory, storage of the large amounts of data which may be required can also be problematic.

It is much more usual to perform calibration at a limited number of points and then use "best fit" procedures to interpolate and/or extrapolate to all parts of the envelope. For example, in the IRceL® IR CO2 sensor (manufactured by City Technology Ltd, Portsmouth, UK) the same generic equation describing the temperature compensation is used for all sensors (written into the host instrument), but with coefficients which are unique to each sensor and carried in an EEPROM located within the sensor housing. At the end of the manufacturing process, the sensor output is measured at four temperatures and four gas concentrations to provide raw calibration data which is converted to fractional absorbance (i.e. the proportion of light in the wavelength band of interest which has been absorbed by the target species) as follows:

$FA = 1 - (gas/(ref*ZCC))$ where

FA=fractional absorbance
gas=gas channel raw data
ref=reference channel raw data
where "gas" and "ref" are derived both from electrical outputs from the signal (gas) and reference channels of the pyroelectric detector (Infratec LIM122B)
ZCC=gas zero constant–the gas/ref ratio stored in EEPROM from the last zero concentration setting point The FA has an inherently nonlinear dependence upon gas concentration at any given temperature, Pyroelectric detectors exhibit significant differences as a function of temperature which limit the accuracy achieved in practice and so require correction. The correction is addressed in the following stages:

Step 1—Account for temperature variations in the zero point by fitting a linear function to the measured values of FA at zero gas concentration:

$ZTFA = FA - ZTC*(temp - ZTP)$ where

ZTFA=zero temperature corrected fractional absorbance
ZTC=zero temperature coefficient (from EEPROM)
Temp=temperature in C (from internal sensor thermistor)
ZTP=actual temperature during zeroing operation Use of a quadratic rather than a linear function for the fit in this step has significant benefits in reducing the overall error.

Step 2—Account for temperature variations in the span point, again using a linear function:

$STFA = ZTFA - STC*(temp - STP)*ZTFA/(SFA + ZTC*(temp - ZTP))$ where

STFA=span temperature corrected fractional absorbance
STC=span temperature coefficient (from EEPROM)
STP=temperature during span operation (measured from internal sensor thermistor and stored on EEPROM for future use)
SFA=span fractional absorbance (from EEPROM)

Step 3—Scale $FA = STFA*SCC$ where

SCC=gas span constant from (EEPROM)

Step 4—Calculate gas concentration using standard growth curves $Conc = (a*FA^2 + b*FA)/(c - FA)$ where Conc=gas concentration
a,b,c=numerical constants defining standard growth curve for the gas species of interest.

Although this approach provides an adequate level of performance for some uses, there is a need for greater measurement accuracy to permit the use of such sensors in more demanding applications. After zero correction, the sequential method above isolates the nonlinearity of the response from the effects of temperature. The process assumes that the FA-concentration curve has the same basic form at all temperatures, whereas there are in fact subtle dependencies on temperature attributable to (for example):

mechanical changes in the sensor altering the light path;
changes in the gas spectrum;
variations in the shape and position of the optical filter pass bands;
spectral changes in the source (bulb) output;
changes in the spectral sensitivity of the detector elements.

In general, existing methods using compensating equations based upon fits to observed dependencies fail to minimize errors across the temperature and concentration range of the sensor.

SUMMARY OF THE INVENTION

In accordance with a first aspect of the present invention, a method of calibrating a gas sensor that generates an output related to the concentration of a sensed gas comprises:

i) obtaining the value of said output or a related value at each of a set of known values of a first variable and at each of a set of known values of a second variable, one of the variables being gas concentration;

ii) for each value of said second variable, determining a first best fit function relating said output or related value to the first variable, each best fit function utilizing at least one coefficient whose value is determined;

iii) for the, or the corresponding, coefficient values from each of the first best fit functions, determined a second best fit function relating said coefficient to the second variable, and replacing the coefficient values in the first best fit functions by the second best fit function; and, iv) repeating step iii) for each further coefficient, if any, in the first best fit functions so as to generate a final function relating said output or related value and said first and second variables.

In the primary application, one of the first and second variables is temperature. We have realised that it is possible to improve temperature compensation by generating functions, linear, quadratic or the like, defining the values of the respective coefficients at different values of the temperature leading to the generation of a truly general function.

Typically, said first variable is gas concentration and the said second variable is temperature. However, the reverse is also possible.

As mentioned above, the other variable will typically be temperature and the following description will assume this to be the case. It will be readily understood by a person of ordinary skill in the art, however, that other variables such as relative humidity could be used and indeed the invention is more generally applicable to more than one such another variable.

Thus, the specific methods described here are for correction of a target measurand in response to a single interference (temperature) but the same method could be applied with multiple interferences. The application of the inventive methods in such cases is rendered simpler if such interferences may be independently measured.

In comparison with the known methods, a general equation is again used to relate the output of the sensor to gas concentration at a fixed temperature. However, the device specific coefficients employed are themselves then rendered functionally dependent on temperature by fitting the same curve type to the sensor output signal at different temperatures.

The coefficients are determined from output signal data describing the behaviour of the sensor across the full operating concentration and temperature ranges. The process generates a mathematical function modelling the two dimensional surface representing the relationship between sensor output, temperature and gas concentration. The coefficients are then used in a generic equation to provide gas concentration outputs optimized for that sensor. By adopting a process which minimizes the errors in fitting the model, the sensor reduces the error in gas measurement for all temperatures and gas concentrations within the ranges employed.

Typically, step ii) will include the step of correcting the first best fit functions for zero point error.

In accordance with a second aspect of the present invention, a method of determining the concentration of a gas using a gas sensor and signal processor in which the gas sensor generates an output related to the concentration of a sensed gas and includes a device for measuring the value of a second variable, the signal processor storing a function which has been determined using a calibration method according to the first aspect of the present invention comprises monitoring the value of the output from the sensor and the value of said second variable; and applying said monitored values to the said stored function to obtain a measure of gas concentration.

As mentioned above, the invention is particularly suited for use with IR gas sensors but is also applicable to other types of gas sensor such as pellistors and electrochemical gas sensors.

BRIEF DESCRIPTION OF THE DRAWINGS

An example of a method according to the invention will now be described with reference to the accompanying drawings, in which:—

DETAILED DESCRIPTION OF THE EMBODIMENTS

Figure 1:
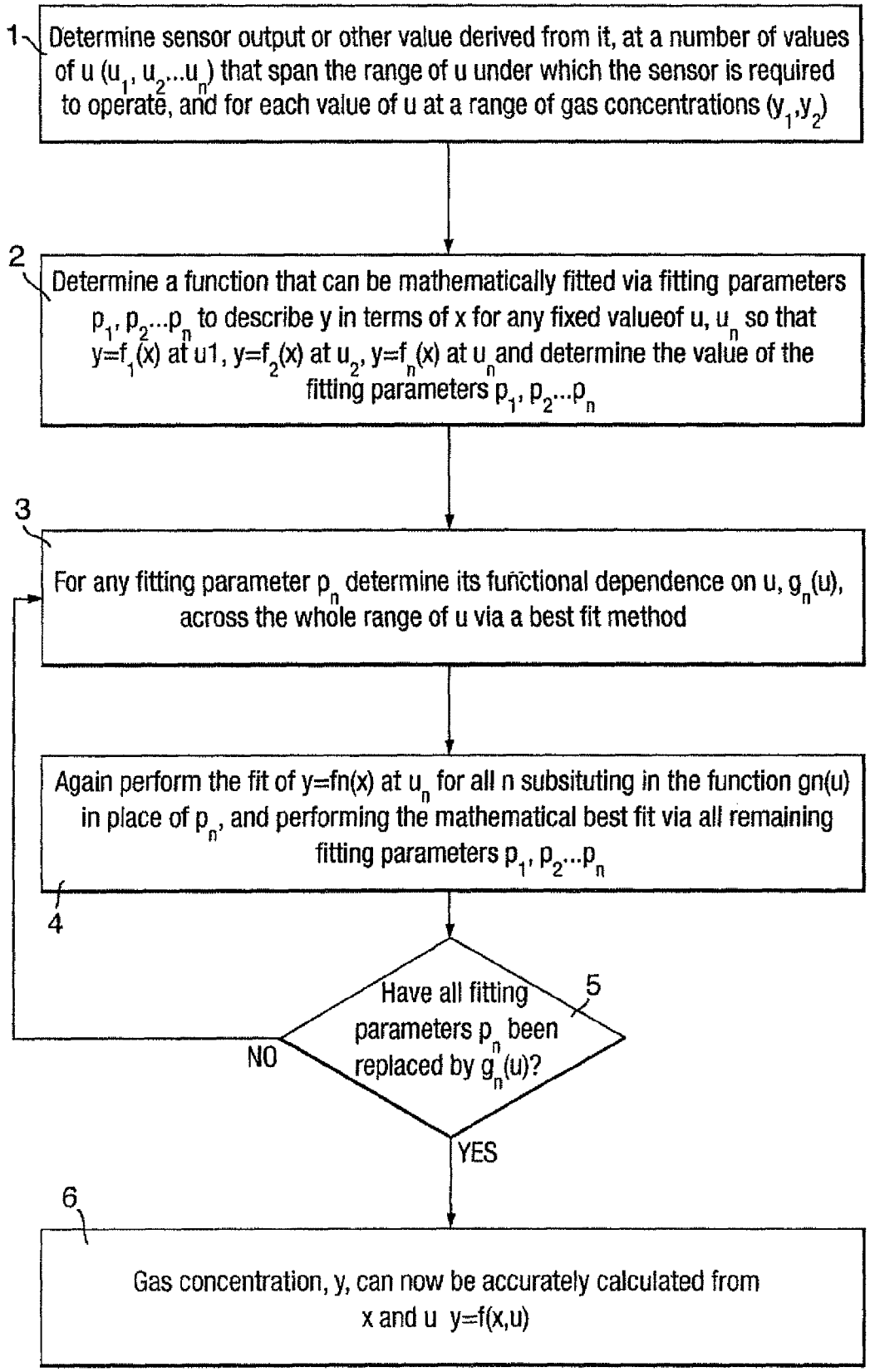
FIG. 1 is a flow diagram illustrating the principle steps of the method.

With reference to FIG. 1, the principles of the method will be described as applied to a gas sensor generating an output or other value (x) related to the concentration of a sensed gas.

In step 1, the value (x) is determined at a number of values of another variable (u) that span the range of u under which the sensor is required to operate, and for each value of u at a range of gas concentrations ($y_1$, $y_2$ ...) that span the range of gas concentrations for which the sensor is required to operate.

In step 2, for each value of u ($u_1$, $u_2$ ...) a function is determined that is a best fit linking y and x in the form:

$$y = f_n(x) \text{ at } u_n$$

where n=1, 2, 3 ...

The functions $f_1$, $f_2$ etc. will have the same form, for example quadratic, and thus involve a number of fitting parameters or coefficients which are determined by the process to achieve the best fit condition.

In step 3, account is taken of the fact that the fitting parameters or coefficients $p_1$, $p_2$ etc. will vary in accordance with the value of u. Thus, in step 3, one of the fitting parameters or coefficients p is selected and the value of that parameter in each of the functions $f_1$, $f_2$ determined in step 2 is obtained and then a best fit function g(u) is determined relating the values of the selected fitting parameter with u.

Each value of the selected fitting parameter in the functions defined in step 2 is then substituted with the function g(u) in step 4 and the remaining parameters or coefficients p are then modified by repeating the best fit process (step 2).

The next parameter or coefficient which has not yet been processed is then processed in accordance with step 3 and a substitution again performed in step 4. This is repeated (step 5) until all parameters have been substituted with corresponding functions g(u) leading to the generation of a single equation of the form y=f(x,u) (step 6).

At this point, gas concentration (y) has been defined in terms of the two variables x,u.

Figure 2:
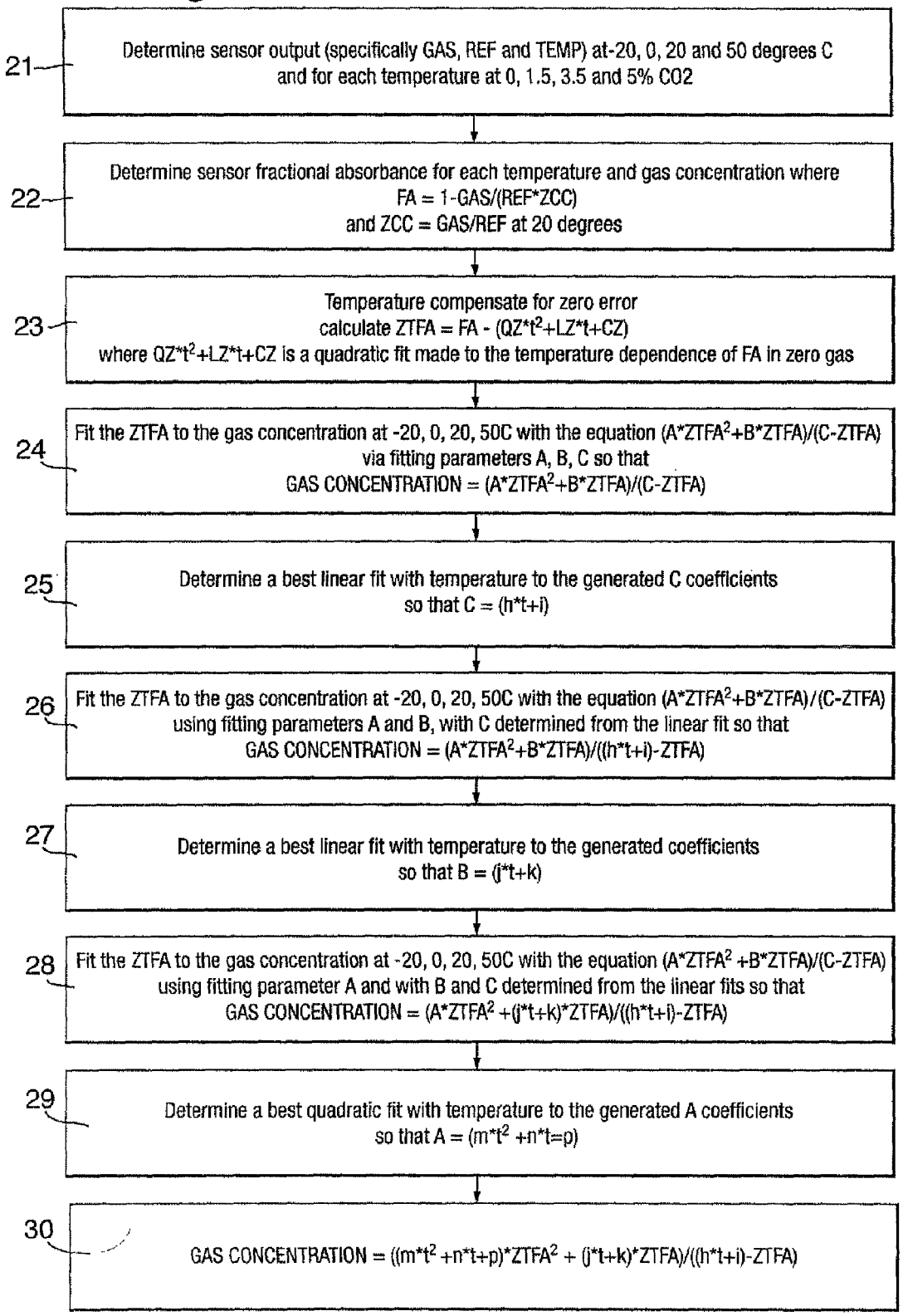
FIG. 2 is a flow diagram similar to FIG. 1 but illustrating the steps of a method when used with an IR gas sensor; and, FIGS. 3 and 4 illustrate the performance of eight IR sensors operating in accordance with a prior art calibration algorithm and a calibration algorithm generated by an example of the method according to the invention respectively.

The process described in general in FIG. 1 will now be described in more detail in conjunction with FIG. 2. This describes how the method is applied in an IR sensor where the additional variable is temperature (t) corresponding to (u) in FIG. 1. In this description, the method is related to the prior art method described above and where appropriate, the same terminology is used for simplicity.

Step 21: Acquire data set in just the same way as under the old method at four concentrations (0, 1.5%, 3.5% and 5.0% CO2) at each of four temperatures (−20.0, 20 and 50 C).

Step 22: Calculate the fractional absorbance (FA) at each point.

Step 23: Use a quadratic fit to normalize the zeros of the four FA concentration curves.

Step 24: Perform a best fit to each of these four zero-normalized FA v concentration curves using:

$$\text{Conc} = (A*(FA^2) + B*(FA))/(C - FA)$$

If a comparison is made between this equation and FIG. 1, it should be noted that the parameters A, B, C correspond to parameters $p_1$, $p_2$, $p_3$.

Also, it should be noted that although the form of this equation is identical to that described in step 4 of the prior art above, the application is quite different. In step 4 of the prior art, the function is used to calculate gas concentration from a set of fit parameters generated by averaging across a large number of sensors at a single temperature (20 C). This data is collected during the development phase and applied globally thereafter. It enshrines the assumption that the behaviour at 20° C. is an adequate representation of the performance across the entire temperature range, which is not adequate if one requires higher levels of accuracy at the extremes or there is large sensor to sensor variation. In the new approach, the function is used to provide the best fit to the performance of a single sensor at a fixed temperature for each of four different temperatures.

Step 25: Generate a linear fit to the C coefficients as a function of temperature (=$\underline{C}$).

Step 26: Repeat step 24 to obtain new values of A(A') and B(B') having fixed C at $\underline{C}$ according to the output of step 25.

Step 27: Generate a linear fit to the B' coefficients as a function of temperature (=$\underline{B}$).

Step 28: Repeat step 24 to obtain new values of A(A") having fixed B and C according to the linear fits in steps 25 and 27 (=$\underline{B}$ and $\underline{C}$).

Step 29: Generate a quadratic best fit to A" values (=$\underline{A}$).

Step 30: This completes the definition of temperature-dependent coefficients $\underline{A}$, $\underline{B}$ and $\underline{C}$ which can then be used in the formula shown in (2) to calculate the best fit concentration value at any temperature in the working range.

This is a very rapid process, easily handled in software. It is readily performed by the same personal computer (PC) which controls the temperature and gas concentrations during the preceding data acquisition. It is also normal to use the same PC to write the relevant information to the EEPROM on the sensor at the end of the process. Thus, it is possible to design self-contained equipment able to perform all relevant calibration functions on a large number of sensors in parallel.

The practical impact of the changes in compensation algorithm upon the sensor design are minimal. There is a small increase in the number of parameters which must be stored in the sensor EEPROM to provide the full compensation capability, but this is unlikely to affect the cost or physical size of the component.

The manufacturing process is also largely unchanged. Data acquisition is the most time consuming and expensive stage of the calibration, but the information required by the improved method is effectively the same as that employed previously. There may be a slight increase in the complexity of the model fitting, since each coefficient in the generic equation is itself now the subject of a best fit.

Figure 3:
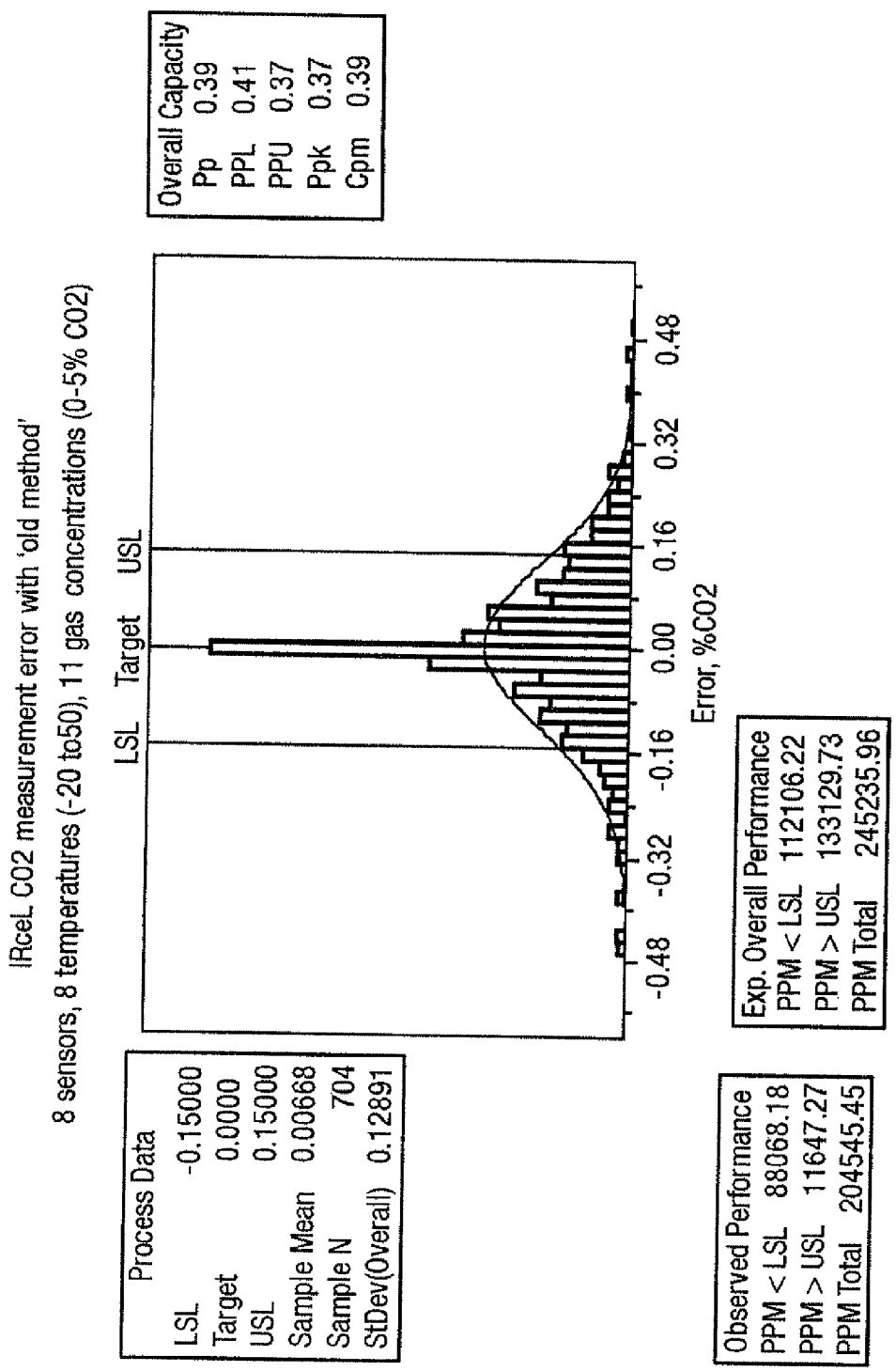
Figure 4:
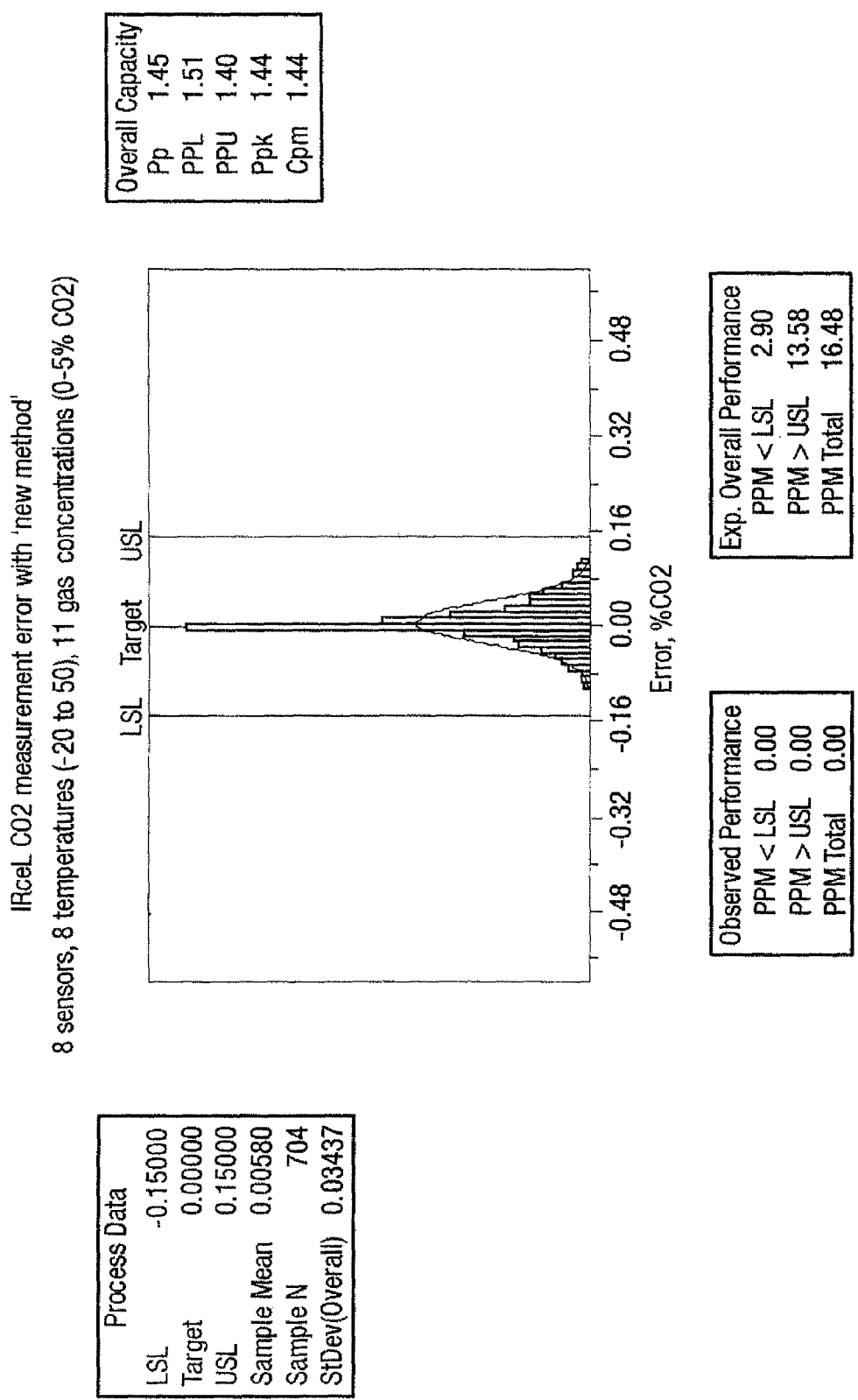

FIGS. 3 and 4 show a comparison of the performance of eight IRceL® CO2 sensors operating under an old compensation algorithm based on the prior art described above, and the new compensation algorithm respectively. The sensors were tested at eight temperatures (10 deg C. intervals between −20 deg C. and +50 deg C.) and 11 gas concentrations (0.5% CO2 intervals between 0.0% and 5.0%), giving a total of 704 reading points from the entire population. The errors resulting from the use of the new and old algorithms derived from this population have then been plotted. The large improvement in accuracy achieved by employing the improved compensation is clearly shown.

Such an improvement is not only important because it increases the accuracy a user may obtain from a particular sensor during a particular test. There are other benefits, particularly in terms of the manufacturer's ability to guarantee a specific level of reproducibility between different sensors (important when, for example, a field exchange is necessary).

Therefore, the invention provides greatly superior field performance with minimal increase in manufacturing costs for the IR sensors in this example.

The principles outlined here may be applied to other sensor technologies which suffer from nonlinear responses, cross sensitivities and/or inter-device variations. In cases where the variations between nominally identical sensors are acceptably small, generic compensations for all sensors of the same type are feasible. Even in such cases, however, the method may still be applied with significant benefit.

We claim:

1. A method of calibrating a gas sensor that generates an output related to the concentration of a sensed gas, the method comprising:
   i) obtaining the value of said output or a related value at each of a set of known values of a first variable and at each of a set of known values of a second variable, one of the variables being gas concentration;
   ii) for each value of said second variable, determining a first best fit function relating said output or related value to the first variable, each best fit function utilizing at least one coefficient whose value is determined;
   iii) for the, or the corresponding, coefficient values from each of the first best fit functions, determining a second best fit function relating said coefficient to the second variable, and replacing the coefficient values in the first best fit functions by the second best fit function; and,
   iv) repeating step iii) for each further coefficient, if any, in the first best fit functions so as to generate a final function relating said output or related value and said first and second variables.

2. A method according to claim 1, wherein one of said first and second variables is temperature.

3. A method according to claim 2, wherein said first variable is gas concentration and said second variable is temperature.

4. A method according to claim 1, wherein the first best fit function is a quadratic function.

5. A method according to claim 1, wherein the second best fit function is a linear or higher order function.

6. A method according to claim 1, wherein the form of the second best fit function for one coefficient is different from that for another coefficient.

7. A method according to claim 1, wherein step ii) includes the step of correcting the first best fit functions for zero point error.

8. A method according to claim 1, wherein at least four known values of each of the first and second variables is used in step (i).

9. A method according to claim 1, wherein the gas sensor comprises an IR sensor.

10. A method of determining the concentration of a gas using a gas sensor and signal processor in which the gas sensor generates an output related to the concentration of a sensed gas and includes a device for measuring the value of a second variable, the signal processor storing a function which has been determined using a calibration method according to claim 1, the method comprising monitoring the value of the output from the sensor and the value of said second variable; and applying said monitored values to the said function to obtain a measure of gas concentration.

* * * * *